United States Patent
Song

(10) Patent No.: US 7,920,268 B2
(45) Date of Patent: Apr. 5, 2011

(54) LONG-RANGE SURFACE PLASMON OPTICAL WAVEGUIDE SENSOR

(75) Inventor: Seok Ho Song, Seoul (KR)

(73) Assignee: IUCF-HYU (Industry-University Cooperation Foundation Hanyang University), Seoul (KR)

( * ) Notice: Subject to any disclaimer, the term of this patent is extended or adjusted under 35 U.S.C. 154(b) by 0 days.

(21) Appl. No.: 12/531,220

(22) PCT Filed: Feb. 28, 2008

(86) PCT No.: PCT/KR2008/001159
§ 371 (c)(1),
(2), (4) Date: Sep. 22, 2009

(87) PCT Pub. No.: WO2008/111745
PCT Pub. Date: Sep. 18, 2008

(65) Prior Publication Data
US 2010/0097611 A1 Apr. 22, 2010

(30) Foreign Application Priority Data

Mar. 14, 2007 (KR) .................. 10-2007-0024782

(51) Int. Cl.
*G01N 21/55* (2006.01)
*H01L 27/18* (2006.01)

(52) U.S. Cl. ........ 356/445; 250/336.2; 385/12; 385/131

(58) Field of Classification Search .......... 356/445–448; 250/336.2; 385/12–14, 147, 129–132; 422/82.05, 422/68.1, 61
See application file for complete search history.

(56) References Cited

U.S. PATENT DOCUMENTS

| | | | | |
|---|---|---|---|---|
| 5,055,265 A | * | 10/1991 | Finlan | 422/82.05 |
| 5,115,336 A | * | 5/1992 | Schildkraut et al. | 359/263 |
| 6,432,364 B1 | | 8/2002 | Negami | |
| 7,043,134 B2 | * | 5/2006 | Berini et al. | 385/147 |
| 7,433,553 B2 | * | 10/2008 | Koo et al. | 385/12 |
| 7,443,507 B2 | * | 10/2008 | Ran et al. | 356/445 |
| 7,583,882 B2 | * | 9/2009 | Guo | 385/131 |
| 7,657,144 B2 | * | 2/2010 | Lee et al. | 385/129 |
| 7,682,566 B2 | * | 3/2010 | Ohtsuka | 422/82.05 |
| 7,718,964 B2 | * | 5/2010 | Frey | 250/336.2 |

FOREIGN PATENT DOCUMENTS

| | | |
|---|---|---|
| JP | 2003/42947 | 2/2003 |
| JP | 2006/234693 | 9/2006 |
| JP | 2006/300726 | 11/2006 |

* cited by examiner

*Primary Examiner* — Sang Nguyen
(74) *Attorney, Agent, or Firm* — Occhiuti Rohlicek & Tsao LLP

(57) ABSTRACT

The present invention provides a long-range surface plasmon optical waveguide sensor which has a reduced loss of an electromagnetic wave, an increased sensitivity and limitation of detection and a high analysis speed, and enables fabrication of a sensor of various sizes such as a small-sized or lightweight system, etc. To this end, the long-range surface plasmon optical waveguide sensor, comprising: a sensor section, wherein the sensor section comprises a substrate, a first dielectric layer stacked on the substrate, a metal thin film stacked on the first dielectric layer, a second dielectric layer stacked on the metal thin film and having a channel penetratingly formed therein in such a fashion that the top surface of the metal thin film is partially exposed into the channel, a metal strip stacked on the second dielectric layer in such a fashion that the underside thereof is partially exposed into the channel, and a third dielectric layer stacked on the metal strip; a light source section for inducing a surface plasmon resonance between the metal thin film and the metal strip; and a detection section for detecting and analyzing a change of light according to the surface plasmon resonance.

16 Claims, 8 Drawing Sheets

[Fig. 1]
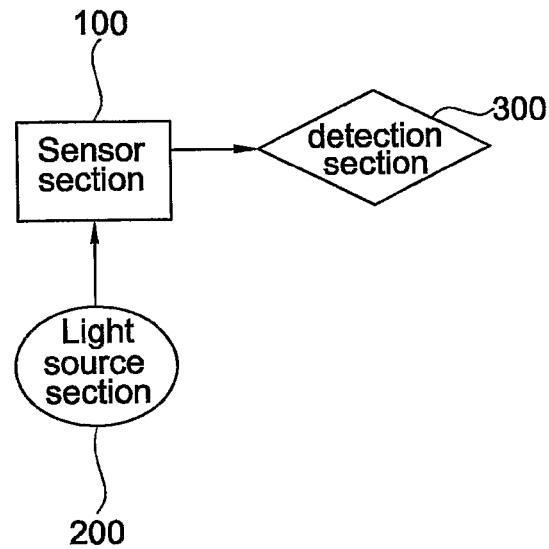
[Fig. 2]
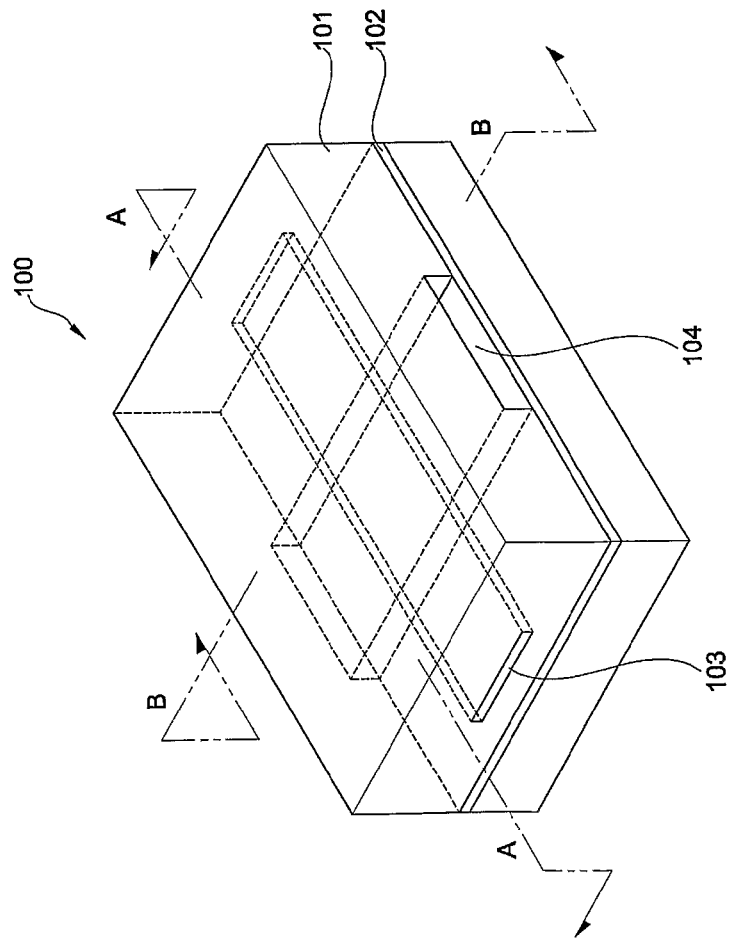

[Fig. 3]
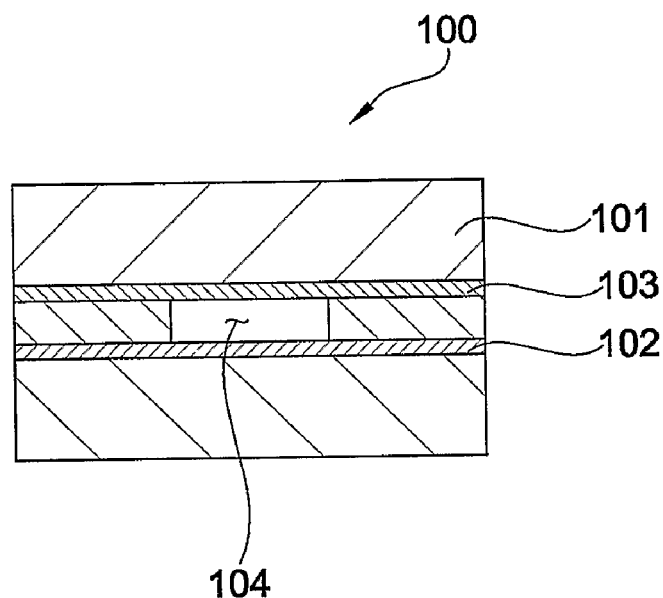
[Fig. 4]
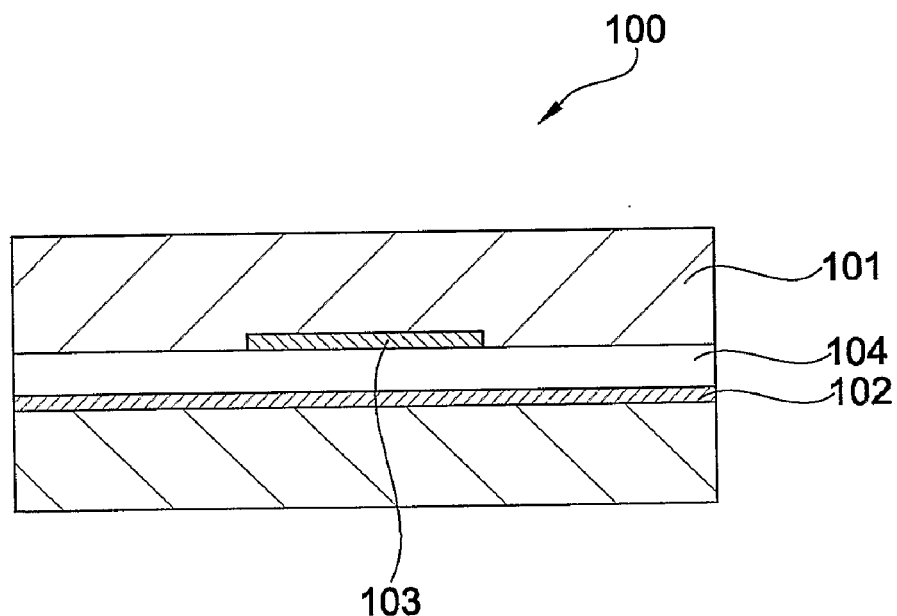

[Fig. 5]
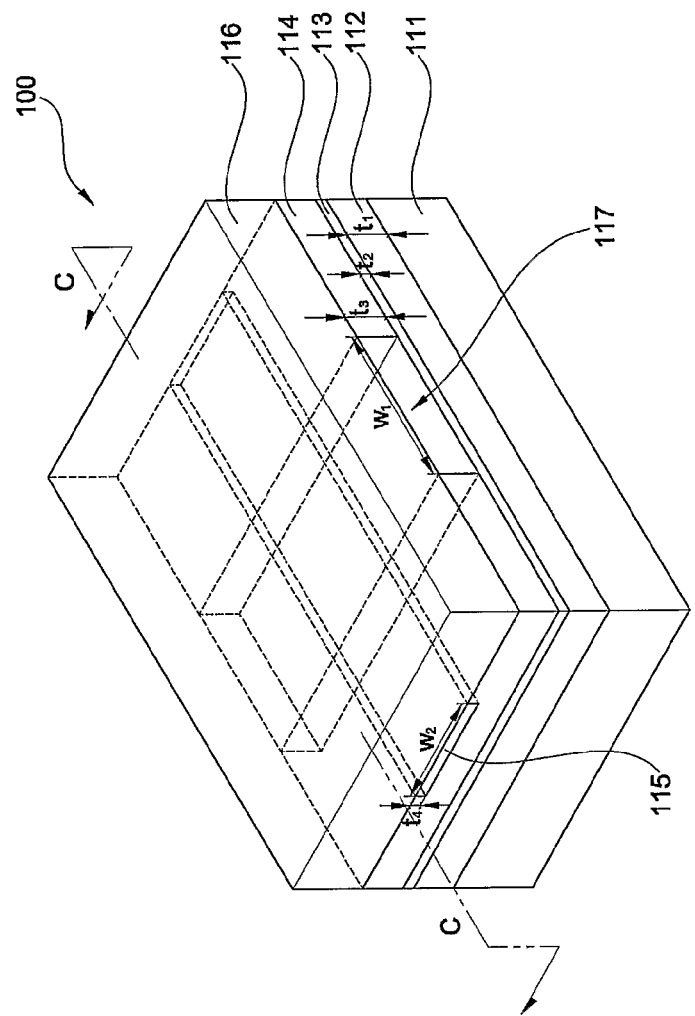
[Fig. 6]
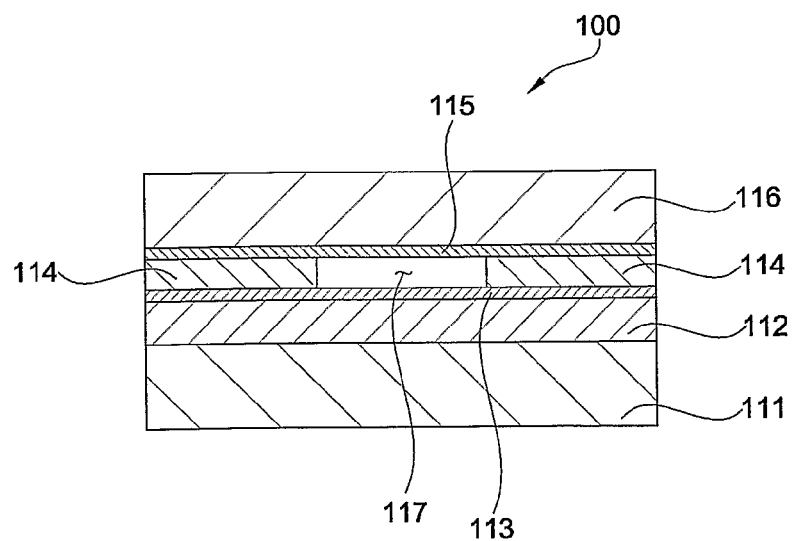

[Fig. 7]
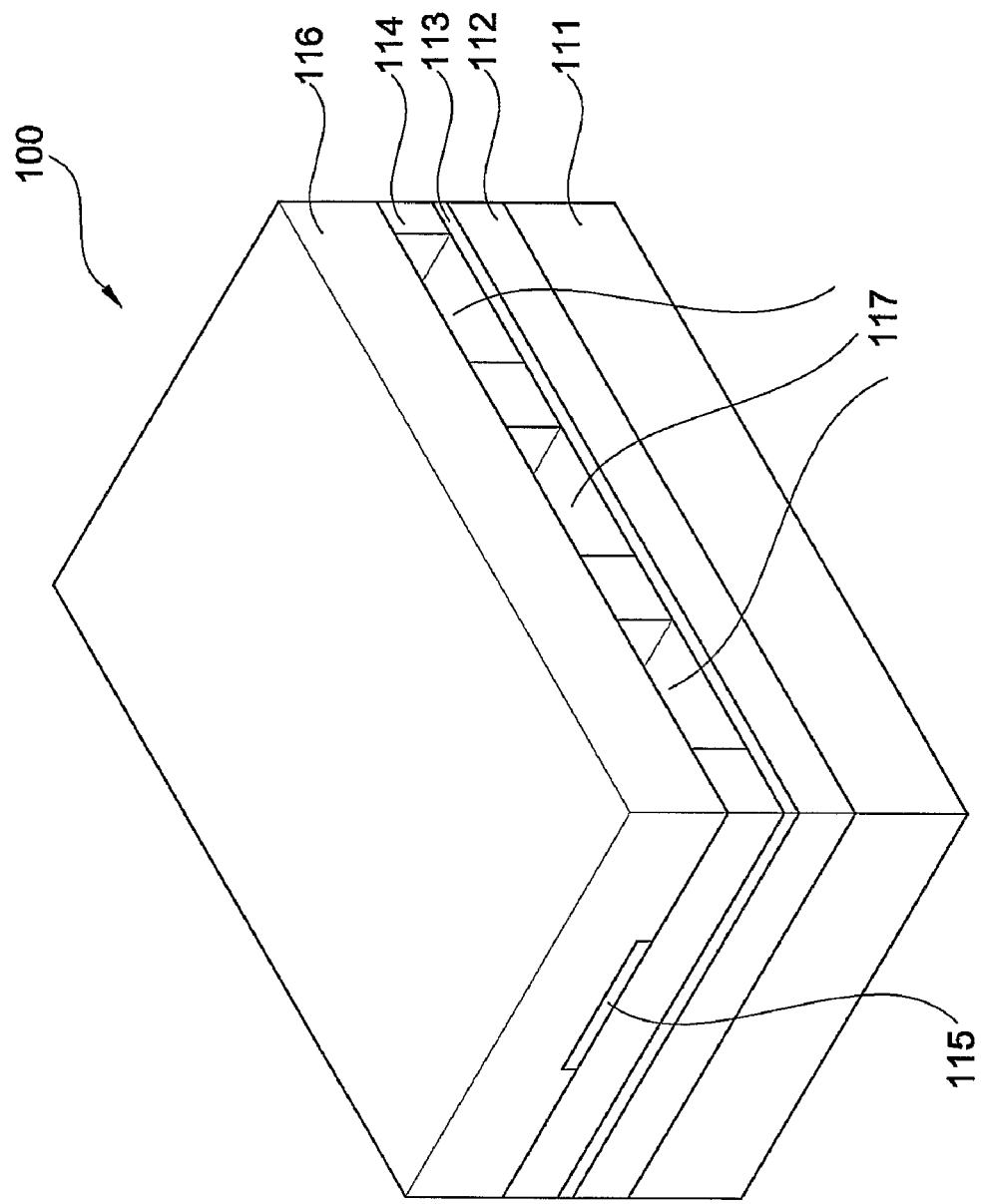

[Fig. 8]
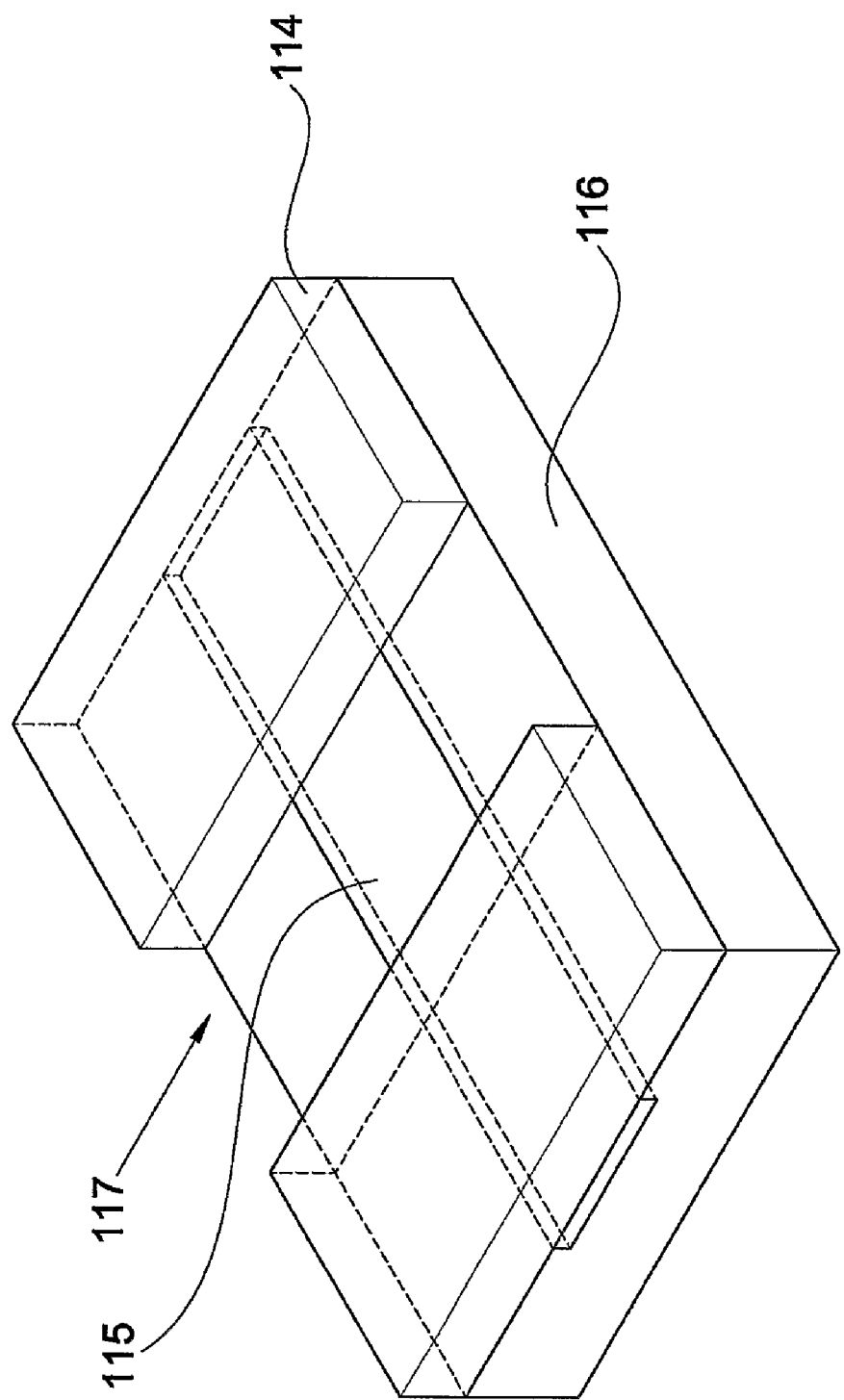

[Fig. 9]
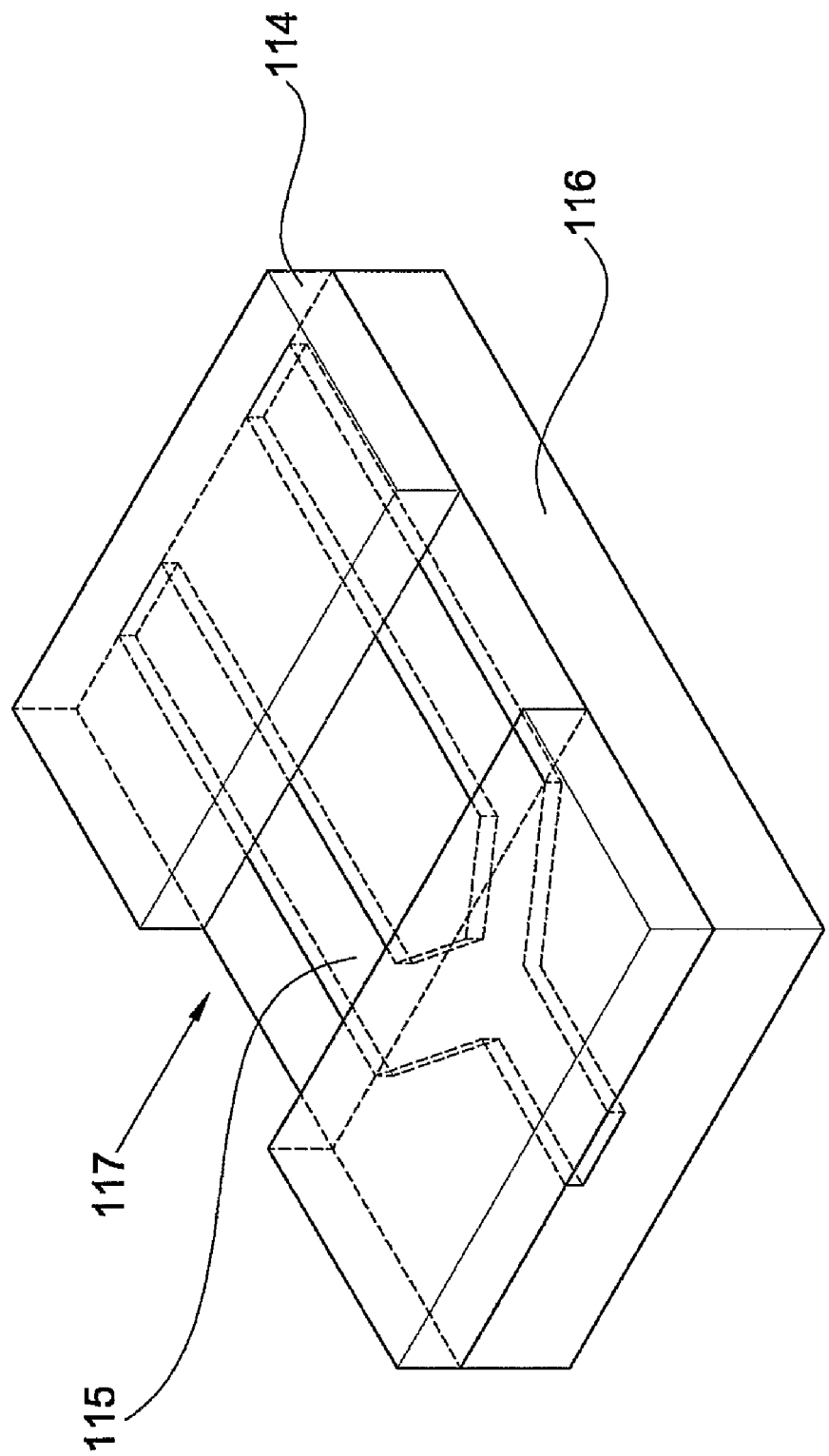

[Fig. 10]
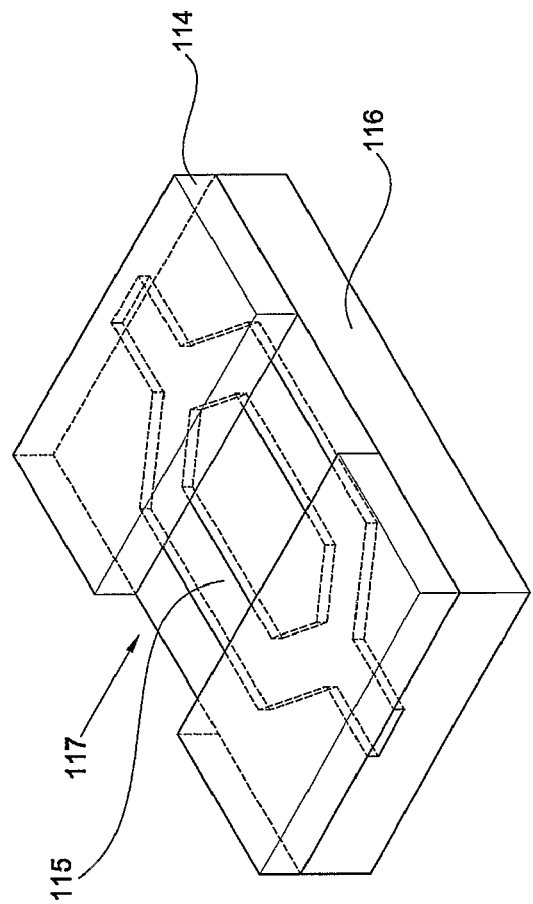
[Fig. 11]
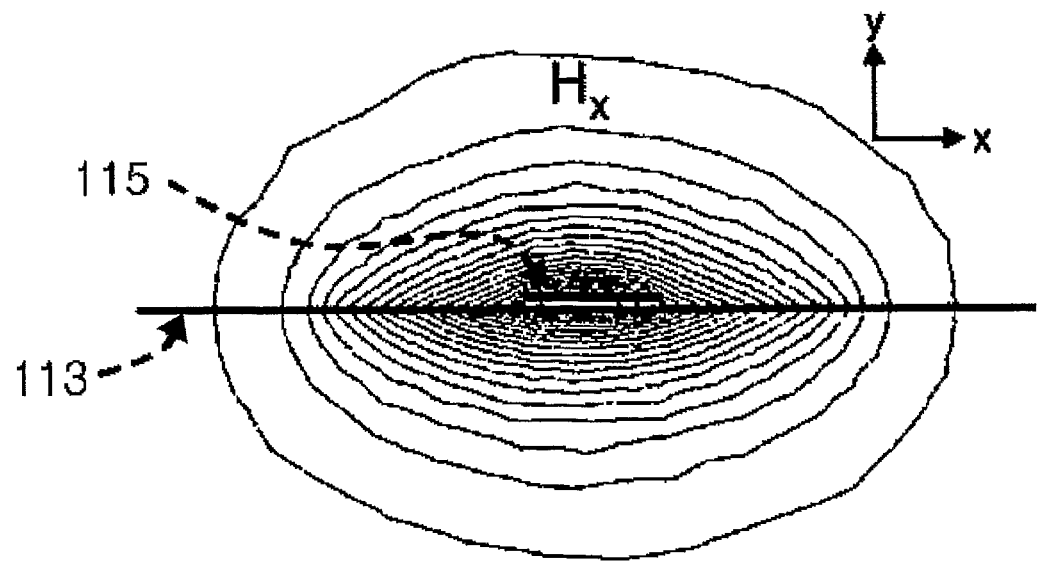

[Fig. 12]
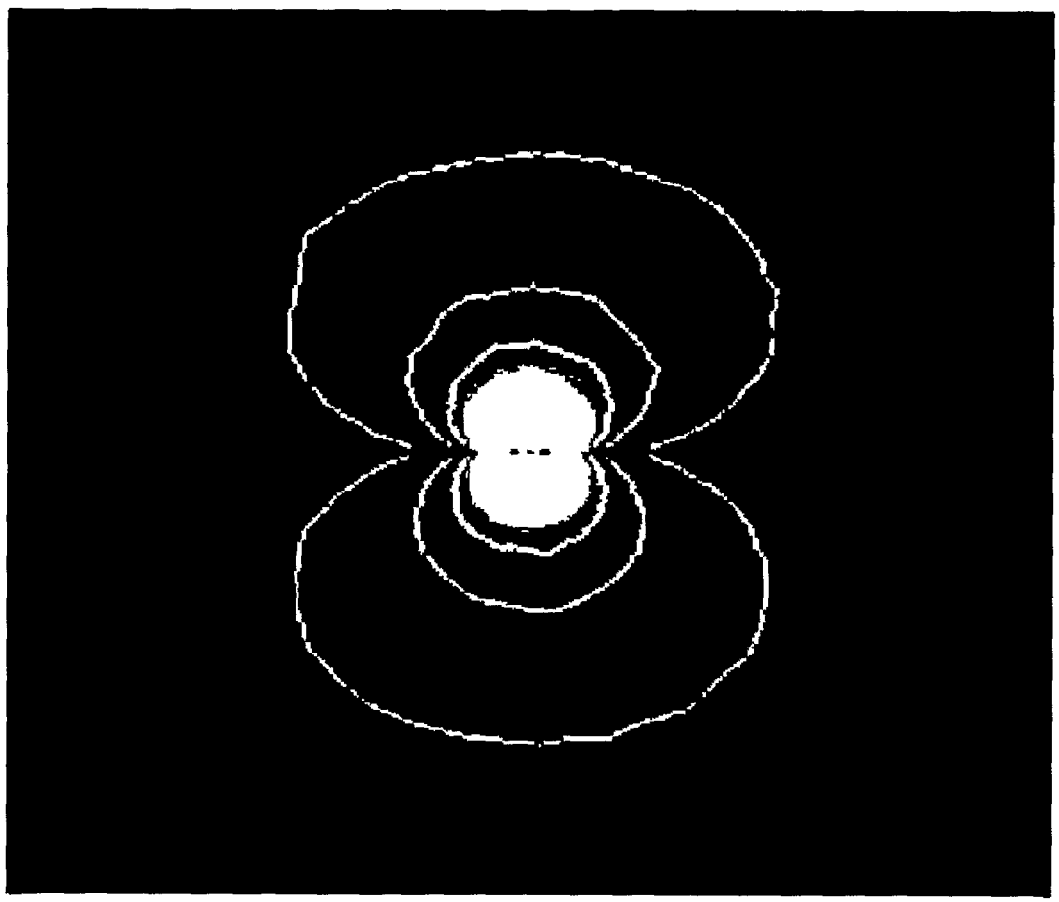

LONG-RANGE SURFACE PLASMON OPTICAL WAVEGUIDE SENSOR

CROSS-REFERENCE TO RELATED APPLICATIONS

This application is the National Stage of International Application No. PCT/KR2008/001159, filed on Feb. 28, 2008, which claims the benefit of Korean Application Serial No. 10-2007-024782, filed on Feb. 28, 2008, the contents of both of the foregoing applications are hereby incorporated by reference in their entirety.

TECHNICAL FIELD

The present invention relates to a long-range surface plasmon optical waveguide sensor, and more particularly, to a long-range surface plasmon optical waveguide sensor which has a reduced loss of an electromagnetic wave, an increased sensitivity and limitation of detection and a high analysis speed, and can be applied as a sensor of various sizes such as a small-sized or lightweight system, etc.

BACKGROUND ART

A surface plasmon refers to a fluctuation in the electron density, i.e., a collective vibration of an electron gas (or plasma) at the boundary surface of two materials of which real number terms of complex dielectric constants have opposite signs to each other. In this case, a surface plasmon wave generated by the surface plasmon is a surface electromagnetic wave propagating along the boundary surface between the two materials, i.e., a metal and a dielectric medium. The surface plasmon exists at the boundary surface between the metal having a negative (−) polarity and the dielectric medium and is excited by electrons or photons accelerated at high speed.

The surface plasmon is a transverse-magnetic (TM) polarized wave and the magnitude of an electric field or a magnetic field forming the wave is decreased exponentially as it goes far away from the metal while being the largest on the metallic surface. Owing to this characteristic, the surface plasmon has widely been used for measurement of the property of the material existing on the metallic surface and the optical constant of the metal itself.

Also, the surface plasmon has lots of merits in its application to a sensor or the like because the electric or magnetic field is concentrated at the proximity of the metal, and is applied as an optical device due to its susceptible response to perturbation of the metallic surface.

Korean Patent Laid-Open Publication No. 2002-15617 proposes a sensor that senses rare earth elements using a surface plasmon resonance. The Korean patent teaches that the sensor is constructed such that a nickel-chromium thin film and a gold thin film are coated on a glass substrate and then a sensing film is coated on the top surface of the thin film layer so as to selectively analyze rare earth elements.

Korean Patent Laid-Open Publication No. 2004-102847 discloses an analysis device that measures the interaction of a biochemical material and a biological material using a surface plasmon resonance phenomenon. The Korean patent teaches that the analysis device can modify the shape of a prism which generates a surface plasmon effect to thereby extend the limitation of measurement.

Korean Patent Laid-Open Publication No. 2004-39553 proposes an immunosensor using a localized surface plasmon phenomenon. The Korean patent teaches that a plurality of nanometer-level metallic structures is formed to be in contact with a specimen on a substrate to thereby further increase sensitivity.

However, the aforementioned patents disclose a structure for generating the surface plasmon in which a metal is formed into a single thin film on a substrate. Such a structure has a disadvantage in that since it allows the surface plasmon to be formed only on the surface of the metallic thin film, the surface plasmon propagates within a very short distance.

DISCLOSURE OF INVENTION

Technical Problem

Accordingly, the present inventor has developed a novel structure in which various dielectric layers are alternately stacked one on top of the other and two very thin metal films are interlacedly formed therebetween, and has found that a long-range surface plasmon is generated along the boundary of the two metal thin films owing to such a structure to thereby increase the propagating distance of the surface plasmon and improve sensitivity of the sensor by virtue of a strong bonding force between the surface plasmons, and as a result has completed the present invention.

Therefore, the present invention has been made in an effort to solve the afore-mentioned problems occurring in the prior art, and it is an object of the present invention to provide a long-range surface plasmon optical waveguide sensor which has a reduced loss of an electromagnetic wave, an increased sensitivity and limitation of detection and a high analysis speed, and enables fabrication of a sensor of various sizes such as a small-sized or lightweight system, etc.

Technical Solution

To accomplish the above object, according to one aspect of the present invention, there is provided a long-range surface plasmon optical waveguide sensor, comprising: a sensor section, wherein the sensor section comprises a block made of a dielectric material, a metal thin film embedded into the block, and a metal strip embedded into the block in such a fashion as to be spaced apart from the metal thin film by a predetermined interval, wherein the block has a channel penetratingly formed therein in such a fashion that the confronting surfaces of the metal thin film and the metal strip are partially exposed into the channel; a light source section for inducing a surface plasmon resonance between the metal thin film and the metal strip; and a detection section for detecting and analyzing a change of light according to the surface plasmon resonance.

In the long-range surface plasmon optical waveguide sensor according to the present invention, preferably, the block is formed in such a fashion that a plurality of materials having different permittivities is stacked one on top of the other.

According to another aspect of the present invention, there is also provided a long-range surface plasmon optical waveguide sensor, comprising: a sensor section, wherein the sensor comprises a substrate, a first dielectric layer stacked on the substrate, a metal thin film stacked on the first dielectric layer, a second dielectric layer stacked on the metal thin film and having a channel penetratingly formed therein in such a fashion that the top surface of the metal thin film is partially exposed into the channel, a metal strip stacked on the second dielectric layer in such a fashion that the underside thereof is partially exposed into the channel, and a third dielectric layer stacked on the metal strip; a light source section for inducing a surface plasmon resonance between the metal thin film and the metal strip; and a detection section for detecting and analyzing a change of light according to the surface plasmon resonance.

The substrate is preferably any one selected from the group consisting of a plastic substrate, a semiconductor substrate and a metal substrate, and each of the first dielectric layer, the second dielectric layer and the third dielectric layer is preferably formed in such a fashion that a plurality of materials having different permittivities is stacked one on top of the other. Also, the second dielectric layer may be formed in such a fashion that a plurality of materials having different permittivities is separately disposed at a plurality of regions divided on the same plane. Each of the first dielectric layer, the second dielectric layer and the third dielectric layer is preferably made of any one selected from the group of consisting of a polyimide-based resin, a polyetherimide resin, a polyetherketone resin, a polyesterimide resin, a silicon-based resin, an acryl-based resin, a polystyrene-based resin, a polycarbonate-based resin, a polyamide-based resin, a polyester-based resin, a phenol-based resin, a polyquinolin-based resin, a polyquinoxaline-based resin, a polybenzoxazole-based resin, a polybenzothiazole-based resin, a polybenzoimidazole-based resin, a polysilane, and a combination thereof.

In addition, the second dielectric layer preferably has a thickness ranging from 10 nm to 10 μm. Also, each of the metal thin film and the metal strip is preferably made of any one selected from the group of consisting of Au, Ag, Cu, Al, In, Sn, Pb, Sb, Ti, V, Cr, Mn, Fe, Co, Ni, Zr, Nb, Mo, Ru, Rh, Pd, Ta, W, Pt and an alloy thereof. At this time, each of the metal thin film and the metal strip preferably has a thickness ranging from 10 nm to 100 nm. Meanwhile, the metal strip preferably has a width ranging from 1 μm to 10 μm. Preferably, the metal strip has any one selected from a linear bar shape, a shape in which a linear bar extends and then is branched off into a Y shape, and a shape in which two linear bars extend toward each other in opposite directions, are branched off into Y shapes, and then the branched bars are interconnected. The metal strip may further comprise a sensing film coated on exposed one side surface thereof.

In the long-range surface plasmon optical waveguide sensor according to the present invention, the channel is preferably formed in plural numbers on the same plane. Further, preferably, the channel has a thickness ranging from 10 nm to 10 μm, and preferably has a width of more than 1 μm.

ADVANTAGEOUS EFFECTS

According to the present invention, it is possible to fabricate a long-range surface plasmon optical waveguide sensor, which can effectively control the propagating characteristics of a long-range surface plasmon. Also, loss of an electromagnetic wave is reduced, sensitivity and limitation of detection are increased and a high analysis speed is ensured. In addition, it is possible to fabricate a sensor of various sizes such as a small-sized or lightweight system, etc.

BRIEF DESCRIPTION OF THE DRAWINGS

The above and other objects, features and advantages of the present invention will be apparent from the following detailed description of the preferred embodiments of the invention in conjunction with the accompanying drawings, in which:

FIG. 1 is a block diagram showing the construction of a long-range surface plasmon optical waveguide sensor according to one embodiment of the present invention;

FIG. 2 is a perspective view showing a sensor section of a long-range surface plasmon optical waveguide sensor according to one embodiment of the present invention;

FIG. 3 is a cross-sectional view taken along the line A-A of FIG. 2;

FIG. 4 is a cross-sectional view taken along the line B-B of FIG. 2;

FIG. 5 is a perspective view showing a sensor section of a long-range surface plasmon optical waveguide sensor according to another embodiment of the present invention;

FIG. 6 is a cross-sectional view taken along the line C-C of FIG. 5;

FIG. 7 is a cross-sectional view showing a modification of the sensor having a plurality of channels formed therein in FIG. 5;

FIGS. 8 to 10 are perspective views showing various implemented shapes of a metallic strip;

FIG. 11 is a diagrammatic view showing the distribution of a magnetic field at a waveguide region during the use of a long-range surface plasmon optical waveguide sensor according to one embodiment of the present invention; and FIG. 12 shows a view showing the distribution of energy in a long-range surface plasmon mode in FIG. 11.

BEST MODE FOR CARRYING OUT THE INVENTION

Reference will now be made in detail to the preferred embodiment of the present invention with reference to the attached drawings. The embodiments of the present invention can be modified in various other forms and should not be construed as being limited by or to the embodiments which will be described in detail hereinafter. Also, in the drawing preferably, the thickness, the size and the like of each element are not to scale and may be exaggerated for sake of explanation and clarity. In this case, throughout the drawings, like reference numerals are used to designate the same or similar elements although these elements are illustrated in different figures. Meanwhile, in case where it is described that one film is disposed "on" another film or a substrate, the one film may directly contact the other film or the substrate, or a third intervening film may be disposed between the one film and the other film or the substrate.

FIG. 1 is a block diagram showing the construction of a long-range surface plasmon optical waveguide sensor according to one embodiment of the present invention.

Referring to FIG. 1, the long-range surface plasmon optical waveguide sensor includes a sensor section 100 for generating a surface plasmon, a light source section 200 for inducing the surface plasmon and a detection section 300 for detecting and analyzing a specimen.

FIG. 2 is a perspective view showing a sensor section of a long-range surface plasmon optical waveguide sensor according to one embodiment of the present invention, FIG. 3 is a cross-sectional view taken along the line A-A of FIG. 2, and FIG. 4 is a cross-sectional view taken along the line B-B of FIG. 2.

The sensor section 100 includes a block 101 formed with a channel 104, a metal thin film 102 and a metal strip 103.

The block 101 has a cubic shape and is made of a dielectric material. The metal thin film 102 and the metal strip 103 are embedded into the block 101.

The metal thin film 102 is made of a metal material and is formed in a flat plate shape having the same area as that of the underside of the block 101.

The metal strip 103 is also made of a metal material, but has a bar or strip shape of a small thickness. The metal strip 103 is disposed in the block 101 in such a fashion as to be spaced, in substantially parallel, apart from the metal thin film 102. In addition, the metal strip 103 has the same length as a longitudinal or transverse length of the underside of the block 101 depending on its arrangement direction. For example, in case where the metal strip 103 is disposed along a longitudinal direction of the underside of the block 101, its length is the same as a longitudinal length of the underside of the block 101.

The block 101 has a channel 104 formed therein. The channel 104 serves as a passageway through which a specimen to be detected passes, and is penetratingly formed in the block 101. In this case, the confronting surfaces of the metal thin film 102 and the metal strip 103 are partially exposed into the channel 104. Further, the channel 104 is oriented to intersect the metal strip 103. For example, as shown in FIG. 2, the channel 104 may be formed to perpendicularly intersect the metal strip 103.

In the meantime, the block 101 may be formed such that a plurality of materials having different permittivities is subsequently stacked one on top of the other. The concrete example thereof will be described in detail in the following embodiment.

FIG. 5 is a perspective view showing a sensor section of a long-range surface plasmon optical waveguide sensor according to another embodiment of the present invention, and FIG. 6 is a cross-sectional view taken along the line C-C of FIG. 5.

The sensor section 100 includes a substrate 111, a first dielectric layer 112 stacked on the substrate 111, a metal thin film 113 stacked on the first dielectric layer 112, a second dielectric layer 114 stacked on the metal thin film 113 and having a channel 117 penetratingly formed therein in such a fashion that the top surface of the metal thin film is partially exposed into the channel 117, a metal strip 115 stacked on the second dielectric layer 114 in such a fashion that the underside thereof is partially exposed into the channel, and a third dielectric layer 116 stacked on the metal strip.

Specifically, the substrate 111 may be any one selected from the group consisting of a plastic substrate, a semiconductor substrate and a metal substrate which are usually used, but is not limited thereto in the present invention.

The first dielectric layer 112 is formed on the entire top surface of the substrate 111. The first dielectric layer 112 employs a material of which a dielectric layer is made. The material of the dielectric layer, which is typically used in the art, can be any one selected from the group consisting of a polyimide-based resin, a polyetherimide resin, a polyetherketone resin, a polyesterimide resin, a silicon-based resin, an acryl-based resin, a polystylene-based resin, a polycarbonate-based resin, a polyamide-based resin, a polyester-based resin, a phenol-based resin, a polyquinolin-based resin, a polyquinoxaline-based resin, a polybenzoxazole-based resin, a polybenzothiazole-based resin, a polybenzoimidazole-based resin, a polysilane, and a combination thereof. Preferably, the resin comprises a fluorine atom, and more preferably may be a polyimide-resin containing fluorine.

The first dielectric layer 112 has a thickness ($t_1$) ranging from 10 nm to 100 nm, and the longitudinal and transverse length of the underside thereof can be determined depending on the need. In this case, the first dielectric layer 112 may have the same size as that of the substrate 111.

The first dielectric layer 112 can be formed through a wet-type coating method or a dry-type coating method known in the art using the resin. The first dielectric layer 112 has a structure in which a single layer is stacked on the substrate 111, or a multi-layered structure in which two or more layers of different materials are stacked one on top of the other on the substrate 111.

The metal thin film 113 is formed on the entire top surface of the first dielectric layer 112.

The metal thin film 113 can be made of a metal material which is typically used. A representative metal material of the metal thin film 113 can be any one selected from the group of consisting of Au, Ag Cu, Al, In, Sn, Pb, Sb, Ti, V, Cr, Mn, Fe, Co, Ni, Zr, Nb, Mo, Ru, Rh, Pd, Ta, W, Pt and an alloy thereof, and preferably uses Au.

The metal thin film 113 has a thickness ($t_2$) ranging from 10 nm to 100 nm.

The metal thin film 113 is formed by using a typical deposition method. A representative deposition method can be any one selected from the group consisting of sputtering ion beam deposition, chemical deposition and plasma deposition.

The second dielectric layer 114 is formed on the metal thin film 113.

The material of the second dielectric layer 114 may be the same as that of the first dielectric layer 112, but may employ any one different from the material of the first dielectric layer among the materials as exemplified above in case where it is needed to make the dielectric constants of the first and second dielectric layers different. In addition, the second dielectric layer 114 preferably has a thickness ($t_3$) ranging from 10 nm to 10 μm.

In the meantime, similarly to first dielectric layer 112, the second dielectric layer 114 can be formed to have a multi-layered structure in which thin films made of different materials are stacked one on top of the other. In this case, the material of the second dielectric layer 114 can employ ones selected from the materials as exemplified above. Likewise, the multi-layered structure in which thin films made of different materials are stacked can be applied to the third dielectric layer 116 which will be described later. Besides, the second dielectric layer 114 may be formed such that it is divided into a plurality of regions on the same plane and then a plurality of materials having different permittivities is separately disposed at the divided regions. In case of a multi-channel sensor having a plurality of channels 117 formed therein, a second dielectric layer 114 having respective channels of different dielectric constants is disposed so that utility of the sensor can be increased depending on the characteristics, the measurement method, etc., of a to-be-measured specimen as will be described later.

Particularly, the second dielectric layer 114 has a certain channel 117 allowing a to-be-analyzed specimen to pass therethrough so as to analyze the specimen using the surface plasmon of the present invention. Each of the channels 117 serves as a passageway for the specimen to be sensed. As shown in FIG. 7, when a plurality of channels 117 are formed on the same plane, a multi-channel sensor system can be configured. Such a multi-channel sensor system can more easily perform analysis of specimens through concurrent measurement or three-dimensioning of various specimens.

At this time, the specimen may be in a gas phase like air or liquid phase, and the shape of a width or a cross-section of the channel can be properly modified depending on or the use of the specimen to be analyzed or the sensor. The channel 117 has a thickness ranging from 10 nm to 10 μm which is same as the thickness ($t_3$) of the second dielectric layer 114, and preferably has a width ($w_1$) of more than 1 μm.

The metal strip 115 is disposed on the second dielectric layer 114 in such a fashion as to be oriented to substantially perpendicularly intersect the channel 117. Such metal strip 115 has a metal bar shape, and is preferably used while changing the width ($w_2$) within the range from 1 μm to 10 μm depending on the specimen so as to adjust a degree of contact with the specimen to be measured.

The metal strip 115 generates a surface plasmon excited electrons or photons accelerated at high speed between the metal strip and the metal thin film 113. The material and the thickness ($t_4$) of the metal strip 115 can be made equal to the material and the thickness ($t_2$) of the metal thin film 113. The material of the metal strip 115 may employ any one different from the material of the metal thin film among the materials of the metal thin film as exemplified above in case where it is needed to allow the dielectric constant of metal strip 115 to be made different from that of the metal thin film 113.

Also, the metal strip 115 may have any one selected from a linear bar shape, a shape in which a linear bar extends and then is branched off into a Y shape, and a shape in which two linear bars extend toward each other in opposite directions, are branched off into Y shapes, and then the branched bars are interconnected. In case of the last shape of the metal strip 114, a specimen passing through the channel 117 comes into contact with the metal strip 115 two times.

FIGS. 8 to 10 are perspective views showing various implemented shapes of a metallic strip wherein the metal strip 115 is viewed from the second dielectric layer 114 in a state where the substrate 111, the first dielectric layer 112 and the metal thin film 113 are excluded. FIG. 8 shows a metal strip 115 having a linear bar shape, FIG. 9 shows a metal strip 115 having a Y-branched shape, and FIG. 10 shows a metal strip 115 having a shape in which two linear bars extend toward each other in opposite directions, are branched off into Y shapes, and then the branched bars are interconnected. This shape can be properly modified selectively by a person having ordinary skill in the art and its variation is also possible in various other forms which are not shown.

In this case, the metal strip 115 can have a sensing film coated on one side surface thereof, preferably an exposed surface contacting the specimen, if necessary. The sensing film can be formed by coating a bio or chemical material known as performing a specific reaction with a specimen to be measured.

As an example, in case where the long-range surface plasmon optical waveguide sensor of the present invention is applied as an immunosensor, a biological material such as an antibody is immobilized on the exposed one side surface of the metal strip 115, and the concentration of an antigen which specifically binds to the antibody is measured to thereby enable implementation of the immunosensor.

As another example, in case where the long-range surface plasmon optical waveguide sensor of the present invention is applied as a rare earth element analysis sensor, an ionophore capable of sensing the rare earth element is mixed with a polymer such as polyvinylchrolide or polyacrylate and the mixture is coated on one side surface of the metal strip 115. Then, the concentration of the rare earth element performing a specific reaction with the ionophore is measured to thereby enable implementation of the rare earth element analysis sensor.

The third dielectric layer 116 is disposed on the metal strip 115, preferably the metal strip 115 is embeddedly disposed into the underside of the third dielectric layer 116. At this time, the third dielectric layer 116 is formed to cover the entire area of the substrate 111. In other words, the third dielectric layer 116 has the same area as that of the underside of the first dielectric layer 112.

The thickness of the third dielectric layer 116 can be made equal to that of the first dielectric layer 112. The third dielectric layer 116 can be made of the same material as that of the first dielectric layer 112, or may employ any one different from the material of the first dielectric layer among the materials as exemplified above so as to make the dielectric constants of the first and third dielectric layers different.

Likewise, the inventive long-range surface plasmon optical waveguide sensor comprises the sensor section 100 that includes the substrate 111, the first dielectric layer 112, the metal thin film 113, the second dielectric layer 114, the metal strip 115, and the third dielectric layer 116.

The light source section 200 connected to the sensor section 100 functions to induce a surface plasmon between the metal thin film 113 and the metal strip 115, and can employ a light source which is typically used.

The light source varies depending on a sensor which it is desired to construct, and examples of the light source can include a halogen lamp, a light emitting diode, a laser or the like. The light source provides an incident light into the sensor section 100.

A specimen measured by the sensor section 100 through the surface plasmon is analyzed by the detection section 300. The detection section 300 is configured to have a function capable of quantitatively or qualitatively measuring a change of wavelength of the surface plasmon propagating by the specimen, a change of mode size, a change of the intensity, etc.

As an example, the sensor section 300 can comprise a photomultiplier, a photodiode, a charge coupled device (CCD) camera capable of imaging a two-dimensional plane, a video camera, a screen or the like. The sensor section 300 may also comprise an optical microscope, a scanning electron microscope, a transmission electron microscope, etc.

In this case, when electrical current is caused to flow into the metal thin film and the metal strip, heat is generated from the metal thin film and the metal strip by electrical resistance as if an electric wire were short-circuited, so that the residue material of the specimen stuck to the surrounding of the metal thin film or the metal strip can be removed, if necessary.

The operation principle of the long-range surface plasmon optical waveguide sensor according to the present invention comprising the above-mentioned elements will be described hereinafter.

First, an electron or photon accelerated at high speed is applied between the metal thin film 113 and the metal strip 115 of the sensor section, a surface plasmon is generated from on the surfaces of the metal thin film 113 and the metal strip 115. Then, a specimen to be analyzed is injected into the channel 117 formed in the second dielectric layer 114, and then detection section 300 quantitatively or qualitatively measures a change of wavelength of the surface plasmon generated from the sensor section, a change of mode size, a change of the intensity, etc.

FIG. 11 is a diagrammatic view showing the distribution of a magnetic field at a waveguide region during the use of a long-range surface plasmon optical waveguide sensor according to one embodiment of the present invention, and FIG. 12 shows a view showing the distribution of energy in a long-range surface plasmon mode in FIG. 11.

In FIG. 11, a magnetic field component Hx is a result calculated through a finite element method.

Referring to FIG. 11, the long-range surface plasmon waveguide propagates light in the form of an electromagnetic wave mode having a concentric shape along the metal thin film and the metal strip. In this case, it can be seen that the magnitude of a magnetic field forming the wave is decreased as it goes far away from the center of the metal thin film and the metal strip. Also, both the metal thin film and the metal strip are sufficiently constrained by the long-range surface plasmon to thereby propagate an electromagnetic wave. In addition, referring to FIG. 12, the distribution of energy of the long-range surface plasmon shows that a bright portion of the center of the figure is a portion where energy is the largest, and the flux density is inclined to be decreased as it goes toward the outer periphery.

It can be seen from the energy distribution of FIGS. 11 and 12 that the central portion where the metal thin film and the metal strip exist appears to be the brightest. At this time, when the to-be-analyzed specimen is injected into the sensor section through the channel 117 and comes into close contact with or is adsorbed onto the metal strip, it reacts with a portion where the energy of the propagating surface plasmon is the largest. At this time, although the amount of specimen is extremely small, it sufficiently affects the propagating surface plasmon, thereby providing an advantage in that sensitivity of the sensor is very excellent. Furthermore, in case of a sensor implemented in the form of the metal thin film and the metal strip as in the present invention, loss of the electromagnetic wave is reduced. Such reduced loss of the electromagnetic wave can further improve sensitivity of the sensor since the surface plasmon is increased in the length interacting with the specimen while propagating.

In this manner, according to the long-range surface plasmon optical waveguide sensor according to the present invention, loss of an electromagnetic wave is reduced, sensitivity and limitation of detection are increased and a high analysis speed is ensured. In addition, it is possible to fabricate a sensor of various sizes such as a small-sized or lightweight system, etc.

Moreover, the channel is formed in plural numbers to realize a multi-channel sensor structure so that analysis of specimens can be more easily performed through concurrent measurement or three-dimensioning of various specimens.

INDUSTRIAL APPLICABILITY

The long-range surface plasmon optical waveguide sensor according to the present invention is applied to various fields including a bio chip such as a DNA chip, a protein chip or the like, an immunosensor, a rare earth element analysis sensor, a gas analysis sensor and the like.

As the present invention may be embodied in several forms without departing from the spirit or essential characteristics thereof, it should also be understood that the above-described embodiments are not limited by any of the details of the foregoing description, unless otherwise specified, but rather should be construed broadly within its spirit and scope as defined in the appended claims. Therefore, all changes and modifications that fall within the metes and bounds of the claims, or equivalence of such metes and bounds are intended to be embraced by the appended claims.

The invention claimed is:

1. A long-range surface plasmon optical waveguide sensor, comprising:
a sensor section, wherein the sensor section comprises a substrate, a first dielectric layer stacked on the substrate, a metal thin film stacked on the first dielectric layer, a second dielectric layer stacked on the metal thin film and having a channel penetratingly formed therein in such a fashion that the top surface of the metal thin film is partially exposed into the channel, a metal strip stacked on the second dielectric layer in such a fashion that the underside thereof is partially exposed into the channel, and a third dielectric layer stacked on the metal strip;
a light source section for inducing a surface plasmon resonance between the metal thin film and the metal strip; and
a detection section for detecting and analyzing a change of light according to the surface plasmon resonance.

2. The long-range surface plasmon optical waveguide sensor according to claim 1, wherein the substrate is anyone selected from the group consisting of a plastic substrate, a semiconductor substrate and a metal substrate.

3. The long-range surface plasmon optical waveguide sensor according to claim 2, wherein each of the first dielectric layer, the second dielectric layer and the third dielectric layer is made of anyone selected from the group of consisting of a polyimide-based resin, a polyetherimide resin, a polyetherketone resin, a polyesterimide resin, a silicon-based resin, an acryl-based resin, a polystylene-based resin, a polycarbonate-based resin, a polyamide-based resin, a polyester-based resin, a phenol-based resin, a polyquinolin-based resin, a polyquinoxaline-based resin, a polybenzoxazole-based resin, a polybenzothiazolebasedresin, a polybenzoimidazole-based resin, a polysilane, and a combination thereof.

4. The long-range surface plasmon optical waveguide sensor according to claim 1, wherein the each of the first dielectric layer, the second dielectric layer and the third dielectric layer is formed in such a fashion that a plurality of materials having different permittivities is stacked one on top of the other.

5. The long-range surface plasmon optical waveguide sensor according to claim 4, wherein each of the first dielectric layer, the second dielectric layer and the third dielectric layer is made of anyone selected from the group of consisting of a polyimide-based resin, a polyetherimide resin, a polyetherketone resin, a polyesterimide resin, a silicon-based resin, an acryl-based resin, a polystylene-based resin, a polycarbonate-based resin, a polyamide-based resin, a polyester-based resin, a phenol-based resin, a polyquinolin-based resin, a polyquinoxaline-based resin, a polybenzoxazole-based resin, a polybenzothiazolebasedresin, a polybenzoimidazole-based resin, a polysilane, and a combination thereof.

6. The long-range surface plasmon optical waveguide sensor according to claim 1, wherein the second dielectric layer is formed in such a fashion that a plurality of materials having different permittivities is separately disposed at a plurality of regions divided on the same plane.

7. The long-range surface plasmon optical waveguide sensor according to claim 6, wherein each of the first dielectric layer, the second dielectric layer and the third dielectric layer is made of anyone selected from the group of consisting of a polyimide-based resin, a polyetherimide resin, a polyetherketone resin, a polyesterimide resin, a silicon-based resin, an acryl-based resin, a polystylene-based resin, a polycarbonate-based resin, a polyamide-based resin, a polyester-based resin, a phenol-based resin, a polyquinolin-based resin, a polyquinoxaline-based resin, a polybenzoxazole-based resin, a polybenzothiazolebasedresin, a polybenzoimidazole-based resin, a polysilane, and a combination thereof.

8. The long-range surface plasmon optical waveguide sensor according to claim 1, wherein each of the first dielectric layer, the second dielectric layer and the third dielectric layer is made of anyone selected from the group of consisting of a polyimide-based resin, a polyetherimide resin, a polyetherketone resin, a polyesterimide resin, a silicon-based resin, an acryl-based resin, a polystylene-based resin, a polycarbonate-based resin, a polyamide-based resin, a polyester-based resin, a phenol-based resin, a polyquinolin-based resin, a polyquinoxaline-based resin, a polybenzoxazole-based resin, a polybenzothiazolebasedresin, a polybenzoimidazole-based resin, a polysilane, and a combination thereof.

9. The long-range surface plasmon optical waveguide sensor according to claim 1, wherein the second dielectric layer has a thickness ranging from 10 nm to 10 μm.

10. The long-range surface plasmon optical waveguide sensor according to claim 1, wherein each of the metal thin film and the metal strip is made of anyone selected from the group of consisting of Au, Ag, Cu, Al, In, Sn, Pb, SJ, Ti, V, Cr, Mn, Fe, Co, Ni, Zr, Nb, Mo, Ru, Rh, Pd, Ta, W, Pt and an alloy thereof.

11. The long-range surface plasmon optical waveguide sensor according to claim 1, wherein each of the metal thin film and the metal strip has a thickness ranging from 10 nm to 100 nm.

12. The long-range surface plasmon optical waveguide sensor according to claim 1, wherein the metal strip has a width ranging from 1 μm to 10 μm.

13. The long-range surface plasmon optical waveguide sensor according to claim 1, wherein the metal strip has anyone selected from a linear bar shape, a shape in which a linear bar extends and then is branched off into a Y shape, and a shape in which t\\O linear bars extend toward each other in opposite directions, are branched off into Y shapes, and then the branched bars are interconnected.

14. The long-range surface plasmon optical waveguide sensor according to claim 1, wherein the metal strip further comprises a sensing film coated on exposed one side surface thereof.

15. The long-range surface plasmon optical waveguide sensor according to claim 1, wherein the channel is formed in plural numbers on the same plane.

16. The long-range surface plasmon optical waveguide sensor according to claim 1, wherein the channel has a thickness ranging from 10 nm to 10 μm, and preferably has a width of more than 1 μm.

* * * * *